US012706197B2

(12) United States Patent
Foin et al.

(10) Patent No.: US 12,706,197 B2
(45) **Date of Patent: *Aug. 11, 2026**

(54) DETERMINATION OF A TREATMENT RESPONSE INDEX

(71) Applicant: KONINKLIJKE PHILIPS N.V., Eindhoven (NL)

(72) Inventors: Nicolas Daniel Marie Foin, Brussels (BE); Arjen Van Der Horst, Tilburg (NL); Manfred Mueller, Eindhoven (NL); Joachim Kahlert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 6 days.

This patent is subject to a terminal disclaimer.

(21) Appl. No.: 18/751,734

(22) Filed: Jun. 24, 2024

(65) Prior Publication Data

US 2024/0347158 A1 Oct. 17, 2024

Related U.S. Application Data

(63) Continuation of application No. 17/288,166, filed as application No. PCT/EP2019/078050 on Oct. 16, 2019, now Pat. No. 12,020,791.

(30) Foreign Application Priority Data

Oct. 26, 2018 (EP) .................................... 18202950
Jan. 24, 2019 (EP) .................................... 19153512

(51) Int. Cl.
*G16H 20/00* (2018.01)
*A61B 5/00* (2006.01)
(Continued)

(52) U.S. Cl.
CPC ......... *G16H 20/00* (2018.01); *A61B 5/02007* (2013.01); *A61B 5/4884* (2013.01);
(Continued)

(58) Field of Classification Search
CPC ........ G16H 20/00; G16H 50/30; G16H 50/20; A61B 5/02007; A61B 5/4884;
(Continued)

(56) References Cited

U.S. PATENT DOCUMENTS

2015/0099989 A1 4/2015 Kobayashi
2016/0095535 A1 4/2016 Hettrick
(Continued)

FOREIGN PATENT DOCUMENTS

RU 2317012 C1 * 2/2008
WO WO-2015102951 A2 * 7/2015 ......... A61B 5/14503
(Continued)

OTHER PUBLICATIONS

International Search Report and Written Opinion of PCT/EP2019/078050, dated Jan. 31, 2020.
(Continued)

*Primary Examiner* — Alaaeldin M. Elshaer

(57) ABSTRACT

The present invention relates to determining a treatment response index. In order to improve and facilitate hypertension treatment procedures, a device (10) for determining a treatment response index is provided that comprises a data input (12), a data processor (14) and a data output (16). The data input is configured to receive a value (18) of at least one first measurement of a physiological parameter of a subject's vasculature under a first condition; and to provide a value (20) of at least one second measurement of the physiological parameter of the vasculature under a second condition. In the second condition, a pre-determined stimulation is provided, and the first condition is non-stimulated or at least differently
(Continued)

stimulated. The data processor is configured to generate a treatment response index. In an example, the data output is configured to provide a classification of the subject into one of at least two groups of subjects, based on the treatment response index.

17 Claims, 7 Drawing Sheets

(51) Int. Cl.
*A61B 5/02* (2006.01)
*G16H 50/20* (2018.01)
*G16H 50/30* (2018.01)

(52) U.S. Cl.
CPC .......... *A61B 5/7275* (2013.01); *G16H 50/20* (2018.01); *G16H 50/30* (2018.01)

(58) Field of Classification Search
CPC .......... A61B 5/7275; A61B 5/20; A61B 5/00; A61B 5/021; G06N 3/08
USPC .......... 705/2, 3
See application file for complete search history.

(56) References Cited

U.S. PATENT DOCUMENTS

2017/0215950 A1* 8/2017 Gross .......... A61N 1/36017
2017/0367756 A1 12/2017 Sliwa
2018/0214212 A1 8/2018 Weiss
2019/0200884 A1* 7/2019 Kuenen .......... A61B 5/02007
2019/0328302 A1* 10/2019 Dubhashi .......... A61B 5/7267
2020/0069196 A1* 3/2020 Hettrick .......... A61B 5/0275

FOREIGN PATENT DOCUMENTS

WO 2016176333 A1 11/2016
WO 2017093926 A1 6/2017
WO 2017198490 A1 11/2017
WO 2017198800 A1 11/2017
WO 2017198867 A1 11/2017
WO 2017198871 A1 11/2017
WO 2018060529 A1 4/2018
WO 2020038757 A1 2/2020

OTHER PUBLICATIONS

Foerster, John et al "A Cold-Response Index for the Assessment of Raynaud's Phenomenon", Journal of Dermatological Science, vol. 45, p. 113-12, 2007.

Toprak, Ugur et al "Follow-up of Treatment response with Dynamic Doppler Ultrasound in Raynaud Phenomenon", Vascular and Interventional Radiology, Dec. 2017.

Finegold, Judith Anne Systematic Evaluation of Hemodynamic Parameters to Predict Hemodynamic Response to renal Artery Denervation, 2016.

* cited by examiner

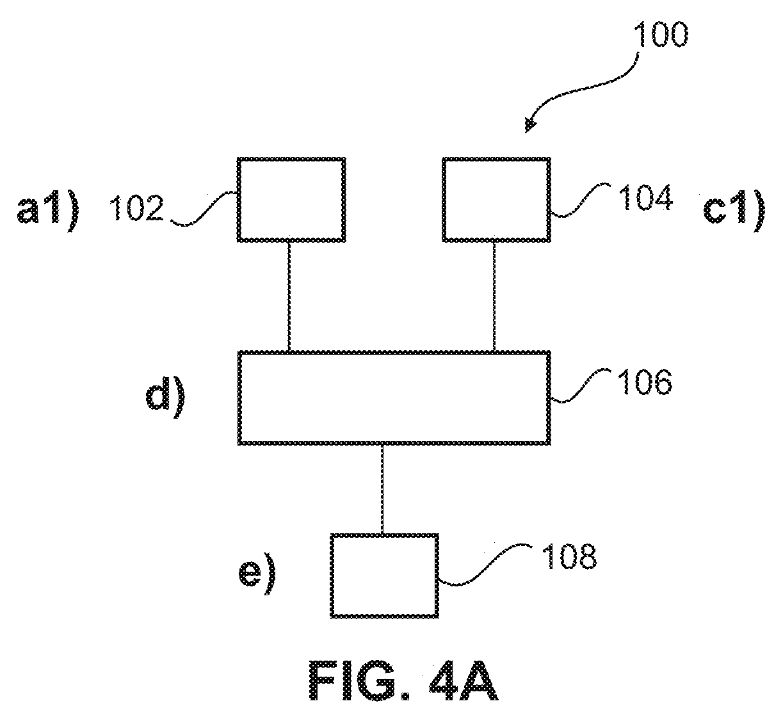
FIG. 4A
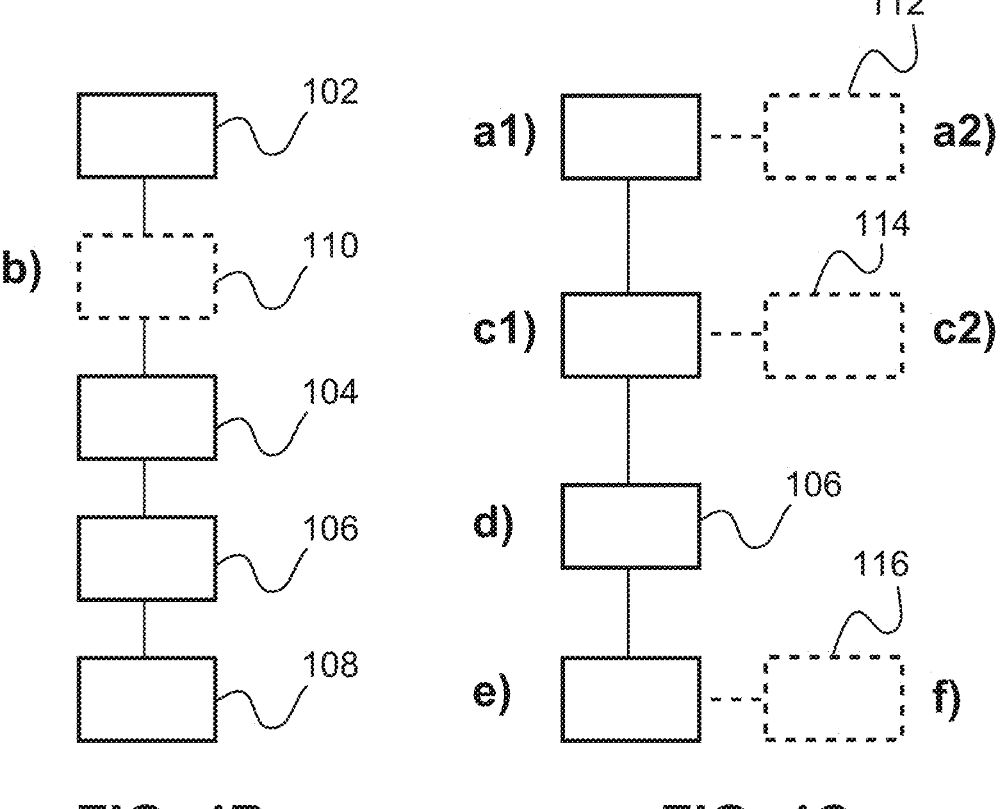
FIG. 4B
FIG. 4C

DETERMINATION OF A TREATMENT RESPONSE INDEX

CROSS-REFERENCE TO PRIOR APPLICATIONS

This application is a continuation of U.S. application Ser. No. 17/288,166, filed on Apr. 23, 2021, now U.S. Pat. No. 12,020,791, which is the U.S. National Phase application under 35 U.S.C. § 371 of International Application No. PCT/EP2019/078050, filed on Oct. 16, 2019, which claims the benefit of European Patent Application No. 18202950.4, filed on Oct. 26, 2018 and European Patent Application No. 19153512.9, filed on Jan. 24, 2019. These applications are hereby incorporated by reference herein.

FIELD OF THE INVENTION

The present invention relates to a device for determining a treatment response index, to a system for determining a treatment response index and to a method for determining a treatment response index, as well as to a computer program element and a computer readable medium.

BACKGROUND OF THE INVENTION

Hypertension is associated with major health risks. One of the causes of hypertension is sympathetic overdrive affecting renal function and blood pressure regulation as it causes peripheral and more specifically renal artery vasoconstriction. Renal denervation (RDN) is a treatment option to block the neural signals and reduce blood pressure in patients with resistant or uncontrolled hypertension. However, the efficacy of renal denervation is very variable between patients. Previous and ongoing renal denervation trials have shown large variability in response between patients undergoing renal denervation. It has been shown that this may make hypertension treatment procedures cumbersome.

SUMMARY OF THE INVENTION

There may thus be a need to improve and facilitate hypertension treatment procedures.

The object of the present invention is solved by the subject-matter of the independent claims; further embodiments are incorporated in the dependent claims. It should be noted that the following described aspects of the invention apply to device, system and method for ascertaining a treatment response index for classifying patients for eligibility for successful treatment, and that the device, system and method are described only exemplarily for determining a renal denervation treatment response index.

According to the present invention, a device for determining a renal response index is provided. The device comprises a data input, a data processor and a data output. The data input is configured to provide a value of at least one first measurement of a physiological parameter of a subject's renal vasculature under a first condition. The data input is also configured to provide a value of at least one second measurement of a physiological parameter of the renal vasculature under a second condition. In the second condition a pre-determined stimulation is provided and the first condition is non-stimulated or at least differently stimulated. The data processor is configured to determine a ratio between the at least one second measurement and the at least one first measurement. The data processor is also configured to generate a renal response index based on the determined ratio and the pre-determined stimulation. The data output is configured to provide the renal response index.

This renal response index provides valuable information regarding a possible renal denervation process. Thus, the renal response index supports hypertension treatment, since renal denervation is one example of measures taken to treat hypertension, as mentioned above. The renal response index provides a facilitated support for the user for making further decision regarding further possible steps. The renal response index is providing objective data to the user in an intuitive way.

The renal response index can also be referred to as renal denervation index or renal denervation response index.

In an example, the first condition is non-stimulated by external stimuli.

In an example, the first condition is less stimulated.

In another example, in the first condition a different kind of stimulation is provided than in the second condition. The different stimulation leads to a different response and can thus provide measurement data applicable for determining an index.

The term "ratio" refers to a calculated relation of the at least two values of the measurements. The term "index" refers to an indication concerning a possible response to a renal treatment. A ratio itself may already implicitly provide information about such response. However, in an example, the index is an improved indication, e.g. a ratio applied to a computation step to provide an intuitive and recognizable index.

In an example, a generalized index/ratio is defined for two measurements V1 and V2 as:

$$(a\ V1+b\ V2)/(c\ V1+d\ V2)$$

This allows ratios such as V1/V2, but also e.g. the difference of the values divided by the average value, e.g. with a=1, b=−1, c=d=0.5).

In an example, more than two values V1, V2, V3, . . . are provided.

According to an example, the data input unit is configured to receive the value of at least one first measurement data and/or the value of at least one second measurement from a device comprising at least one of the group of an intravascular device and an non-invasive external device comprising an extravascular imaging device.

In an example, the data input unit is configured to receive the value of at least one first measurement data and/or the value of at least one second measurement from an intravascular device.

In another example, the data input unit is configured to receive the value of at least one first measurement data and/or the value of at least one second measurement from an extravascular imaging device.

According to an option, provided in addition or alternatively, the physiological parameter is at least one of the group of vessel blood pressure, pulse wave velocity, vessel impedance, vessel blood flow, vessel blood flow velocity and vessel geometry.

According to an example, the pre-determined stimulation for the second condition is provided as at least one of the group of a physical manoeuver, a pharmaceutical stimulus and an electrical stimulus.

According to an option, provided in addition or alternatively, the stimulation results in hemodynamic alteration. The renal response index is determined as at least one of the group of a vascular impedance alteration index, a renal flow alteration index, a pulse propagation alteration index and a pulse reflection alteration index.

According to an example, the data processor is further configured to determine if the generated renal response index is below or above a pre-determined threshold value, which threshold value is indicating a possible suitability for renal denervation. Further, the data output is configured to provide the threshold indicator. Still further, the renal response index provides a stratification of individuals in at least two groups, with one of the group representing subjects not likely to respond well to renal denervation therapy.

The threshold value is based on empiric data, e.g. retrieved from clinical studies.

According to an example, the data input is configured to provide values of the first measurement under the first condition for the left renal artery and for the right renal artery. The data input is also configured to provide values of the second measurement under the second condition for the left renal artery and for the right renal artery.

In a first option, the data processor is configured to i) determine a ratio between the second measurement and the first measurement separately for each of the left and right renal arteries, and to generate a respective index separately for each of the left and right renal arteries.

In a second option, provided in addition or alternatively, the data processor is configured to ii) determine an average ratio between the second measurement and the first measurement for the left and right renal arteries, and to generate the index based on the average ratio.

In a third option, also provided in addition or alternatively, the data processor is configured to iii) determine an average ratio between the second measurement and the first measurement for the left and right renal arteries, and to generate the index based on a difference between the left and right measurement divided by the average ratio.

According to the present invention, also a system for determining a renal response index is provided. The system comprises a measuring arrangement with at least one sensor element configured to measure at least one physiological parameter of the subject's renal vasculature. The system also comprises a device for determining a renal response index according to one of the preceding examples. The system comprises a display device. The measuring arrangement is configured to provide the value of at least one first measurement and the value of at least one second measurement to the classifying device. The display device is configured to display at least the renal response index generated by the classifying device.

According to an example, the measuring arrangement comprises an intravascular device with at least one sensor element configured to be inserted into a vascular structure of a subject and to measure the at least one physiological parameter of the subject's renal vasculature.

In an example, the intravascular device is a catheter or guide wire with a sensor in the tip (i.e. distal end) region.

According to an example, the system also comprises a stimulation unit configured to provide electrical stimuli and/or to provide pharmaceutical stimuli by drug supply. In an option, the stimulation unit is integrated with the measuring arrangement.

According to an example, the system also comprises an ablation unit configured to provide renal ablation. In an option, the ablation unit is integrated with the measuring arrangement.

According to the present invention, also a method for determining a renal response index is provided. The method comprises the following steps:

a1) providing a value of at least one first measurement of a physiological parameter of a subject's renal vasculature under a first condition;

c1) providing a value of at least one second measurement of a physiological parameter of the renal vasculature under a second condition;

wherein in the second condition a pre-determined stimulation is provided and in the first condition, the subject's renal vasculature is non-stimulated or at least differently stimulated than in the second condition;

d) determining a ratio between the at least one second measurement and the at least one first measurement, and generating a renal response index based on the determined ratio and the pre-determined stimulation; and e) providing the renal response index, and/or providing a classification into at least two groups of subjects, the classification based on the renal response index.

According to an aspect, a response to one or more certain actions is measured and the responses are quantified and set in relation to a baseline index to provide an indication of the physiological suitability of a subject for a possible further treatment.

According to an aspect, renal vascular parameters are taken as an indicator for the suitability for renal denervation. In order to provide an approach for assessment, one or more physiological parameters that relate to the renal vascular structure, i.e. the vasculature, is/are measured. At least two measurements are provided, from which at least one relates to a stimulated condition and at least one other relates to a non- or less or differently stimulated condition. The two values can then be taken for calculating an index. The index can then provide some objective assessment if the particular subject will most likely respond to renal denervation or not.

According to an aspect, it is provided a system and an endovascular device with a sensor to measure and display a physiological parameter (e.g. pulse wave velocity and/or resistance/impedance) in one or both renal vessels.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 4*a* shows basic steps of an example of a method for determining a renal response index.

FIG. 4*b* shows another example of the method.

FIG. 4*c* shows a further example of the method.

DETAILED DESCRIPTION OF EMBODIMENTS

Figure 1:
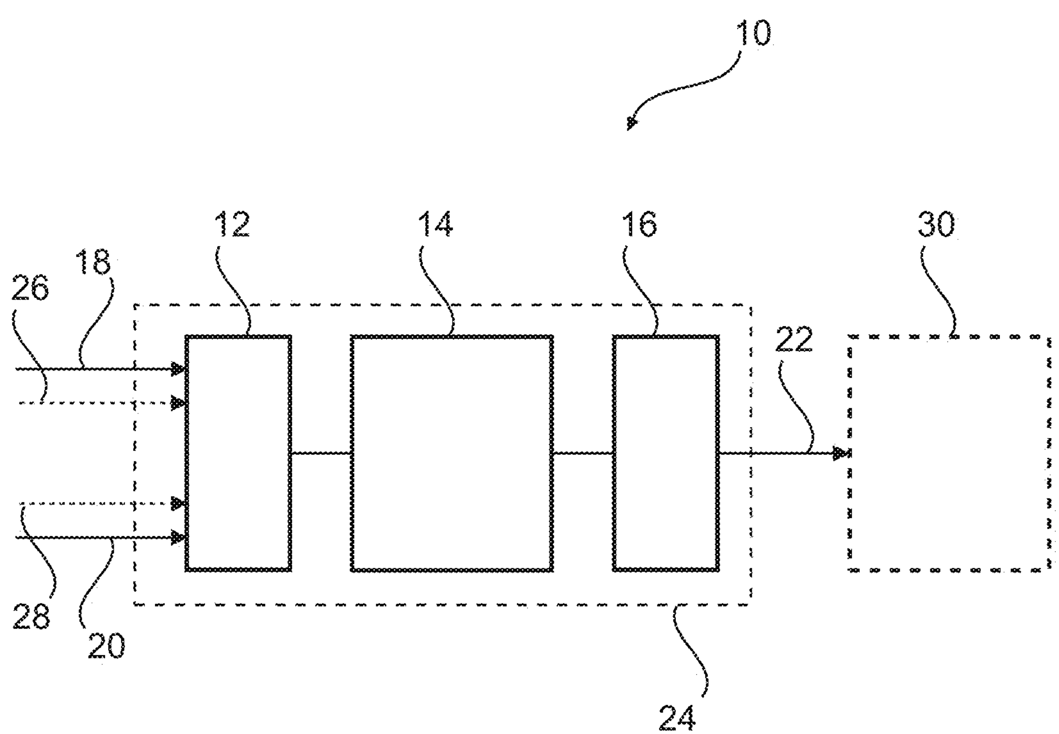
FIG. 1 schematically shows an example of a device for determining a renal response index.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The term "subject" may also be referred to as individual. The "subject" may further also be referred to as patient, although it is noted that this term does not indicate whether any illness or disease is actually present with the subject.

FIG. 1 schematically shows an example of a device 10 for determining a renal response index, comprising a data input 12, a data processor 14 and a data output 16. The data input 12 is configured to receive a value 18 of at least one first measurement of a physiological parameter of a subject's renal vasculature under a first condition. The data input 12 is also configured to receive a value 20 of at least one second measurement of a physiological parameter of the renal vasculature under a second condition. In the second condition, a pre-determined stimulation is provided and the first condition is non-stimulated, or at least differently stimulated. The data processor 14 is configured to determine a ratio between the at least one second measurement and the at least one first measurement. The data processor 14 is also configured to generate a renal response index 22 based on the determined ratio and the pre-determined stimulation. The data output 16 is configured to provide the renal response index 22.

A frame 24 is indicated with a hashed line illustrating that the device 10 for determining a renal response index can be provided as a structural entity, like in a housing, or as several components.

In an option, the data output 16 is configured to provide a classification into at least two groups of subjects, based on the determined renal response index.

The device for determining a renal response index can also be referred to as "classification device for determining a renal response index".

The index is a renal response index of a subject, i.e. an index if and how the subject will respond to a renal denervation procedure.

The data input 12 can also be referred to as data input unit or input unit. The data processor 14 can also be referred to as data processing unit or processing unit. The data output 16 can also be referred to as data output unit or output unit.

The first and second measurements are done under different conditions. The first condition is so-to-speak the normal condition where the subject is under minimum external influence, and any possible stimulation is e.g. kept to a minimum. The second condition is provided as a so-to-speak exceptional condition where the subject is influenced in such a way that stimulation is provided that can result in different physiological behavior and thus in different physiological parameter. The (possible) stimulation is pre-determined to allow comparison of the resulting measurements.

In an example, the first condition is a non-stimulated condition and the second condition is stimulated.

In another example, the first condition is stimulated and the second condition is a non-stimulated condition.

In another example, the first condition is a stimulated condition with a first stimulation, and the second condition is a stimulated condition with a second stimulation, but the second stimulation is larger than the first stimulation.

In another example, the first condition is a stimulated condition with a first stimulation, and the second condition is a stimulated condition with a second stimulation, but the first stimulation is larger than the second stimulation.

In another example, in one of the first and the second condition, a primary pre-determined stimulation is provided, and in the other one of the first and the second condition, a secondary stimulation is present, wherein the primary pre-determined stimulation is different that the secondary stimulation. The stimulation relates to a stimulation effect on the renal vasculature.

In a further example, multiple stimuli are provided which are different from each other and the relative changes due to different stimuli are considered.

In an example, the stimulation is provided as a stimulation of the renal vasculature.

In another example, the stimulation is provided as a stimulation of other parts of the subject that result in an effect on the renal vasculature, but without stimulating the renal vasculature directly.

The first and the second measurements are provided in sequence, e.g. the second condition scenario is directly following the first condition scenario or vice versa, i.e. the first condition scenario can also directly follow the second condition scenario. The term "directly" refers to a minimum time span provided inbetween.

In an example, the time span between the two measurements may for example be necessary to prepare the stimulation, i.e. the application of the stimulation, such as a physical activity or drug supply or some other treatment, or a combination thereof.

In an example, the index is based on two quasi-static measurements.

In another example, the index is determining the response time and/or transition time such that the "time span" is of relevance.

The determination of the physiological parameters are objective measurements. The index derived from this data is also an objective evaluation, since in an example, the renal response index is based on clinical data. As an example, physiological parameters are acquired for a plurality of cases and the respective outcome of the renal denervation treatments is assessed to identify a threshold value for the renal response index. The threshold may also be provided in form of a range. For example, a range may be identified which has proven to lead to certain positive (or negative) results of renal denervation. In a further example, a range may be defined in which a clear assignment to one of the two groups is not possible and further steps are recommended to make a founded assessment.

The renal response index is providing an objective assessment of a subject's situation in terms of a possible treatment of renal denervation. The renal response index thus supports the physician in his/her therapy decision. The renal response index provides a relation of statistic data to the present situation as presented by the objective measurements of the physiological parameter. Of course, the index is based on empirical data and is validated by clinical studies.

The index, for example provided in the form of a threshold value or threshold range, provides information if a subject going through renal denervation procedure will show positive effects of such renal denervation procedure.

In an example, the renal response index relates to a suitability of the respective subject for renal denervation procedures.

In an example, the data input unit 12 is configured to receive the value of at least one first measurement data and/or the value of at least one second measurement from a device (not shown in detail) comprising at least one of the group of an intravascular device and an non-invasive external device comprising an extravascular imaging device. The physiological parameter is at least one of the group of vessel blood pressure, pulse wave velocity, vessel impedance, vessel blood flow, vessel blood flow velocity and vessel geometry.

It is noted that the data input unit 12 being configured to receive the data, i.e. the values from a device, like an intravascular device or an extravascular imaging device, is provided as an option. It is noted that the type of physiological parameter is also provided as an option, i.e. in addition or alternatively.

In an example, the vessel impedance is referred to as flow resistance. The flow resistance relates to the downstream resistance. It is noted that this does not refer to the resistance in the vessel where the measurement takes place.

In an example, the first and second measurement relate to the same physiological parameter.

In another example, the first and second measurement relate to different physiological parameters.

The pre-determined stimulation for the second condition is provided as at least one of the group of a physical manoeuver, a pharmaceutical stimulus and an electrical stimulus.

The stimulation results in hemodynamic alteration, and the renal response index is determined as at least one of the group of a vascular impedance alteration index, a renal flow alteration index, a pulse propagation alteration index and a pulse reflection alteration index.

The pre-determined stimulation for the second condition being of the group of the pre-determined stimulation for the second condition is provided as an option.

The stimulation resulting in hemodynamic alteration, and the renal response index being determined as at least one of the group of a vascular impedance alteration index, a renal flow alteration index, a pulse propagation alteration index and a pulse reflection alteration index, are also provided as an option.

The vascular impedance alteration index can also be referred to as resistance alteration index. The pulse propagation alteration index can also be referred to as propagation index. The pulse reflection alteration index can also be referred to as reflection index.

In an example, a combination of these indices is provided to determine the renal response index.

The data processor 14 may further be configured to determine if the generated renal response index is below or above a pre-determined threshold value, which threshold value is indicating a possible suitability for renal denervation. The data output 16 is configured to provide the threshold indicator. The renal response index provides a stratification of individuals in at least two groups, with one of the group representing subjects not likely to respond well to renal denervation therapy, i.e. into one group that responds better to renal denervation therapy than the other group.

In an example, provided as an option, the data output 16 is configured to provide the value of the at least one first measurement, and/or the value of the at least one second measurement.

In an example, shown as option in FIG. 1 by hashed lines, the data input 12 is configured to receive a further value 26 of a further first measurement of a further physiological parameter of the subject's renal vasculature under the first condition. The data input 12 is also configured to receive a further value 28 of a further second measurement of a further physiological parameter of the renal vasculature under the second condition. The data processor 14 is configured to determine a ratio between the further second measurement and the further first measurement. The data processor 14 is also configured to generate the renal response index based on the determined ratio between the at least one second measurement and the at least one first measurement, the determined ratio between the further second measurement and the further first measurement and the pre-determined stimulation.

In an example, each measurement delivers an index. Multiple measurements/stimuli enable to determine an index based on pre-determined indices (measured under different conditions).

In an example, shown as an option, a display 30 is provided configured to show the renal response index. The display 30 can be provided as an integrated display unit.

In another example, the display 30 is configured to display the value of the at least one first measurement and/or the value of the at least one second measurement.

In an example, not further shown, the data input 12 is configured to provide values of the first measurement under the first condition for the left renal artery and for the right renal artery. The data input 12 is also configured to provide values of the second measurement under the second condition for the left renal artery and for the right renal artery.

In an option, the data processor 14 is configured to i) determine a ratio between the second measurement and the first measurement separately for each of the left and right renal arteries, and to generate a respective index separately for each of the left and right renal arteries.

In addition, or alternatively, the data processor 14 is configured to ii) determine an average ratio between the second measurement and the first measurement for the left and right renal arteries, and to generate the index based on the average ratio.

In addition, or alternatively, the data processor 14 is configured to iii) determine an average ratio between the second measurement and the first measurement for the left and right renal arteries. The data processor 14 is also configured to generate the index based on a difference between the left and right measurement divided by the average ratio.

In an example, both renal vessels are treated with a similar renal denervation procedure based on the outcome.

In another example, the renal vessels are treated with a different renal denervation procedure based on the outcome.

In another example, only one of the renal vessels is treated with a renal denervation procedure based on the outcome.

Figure 2:
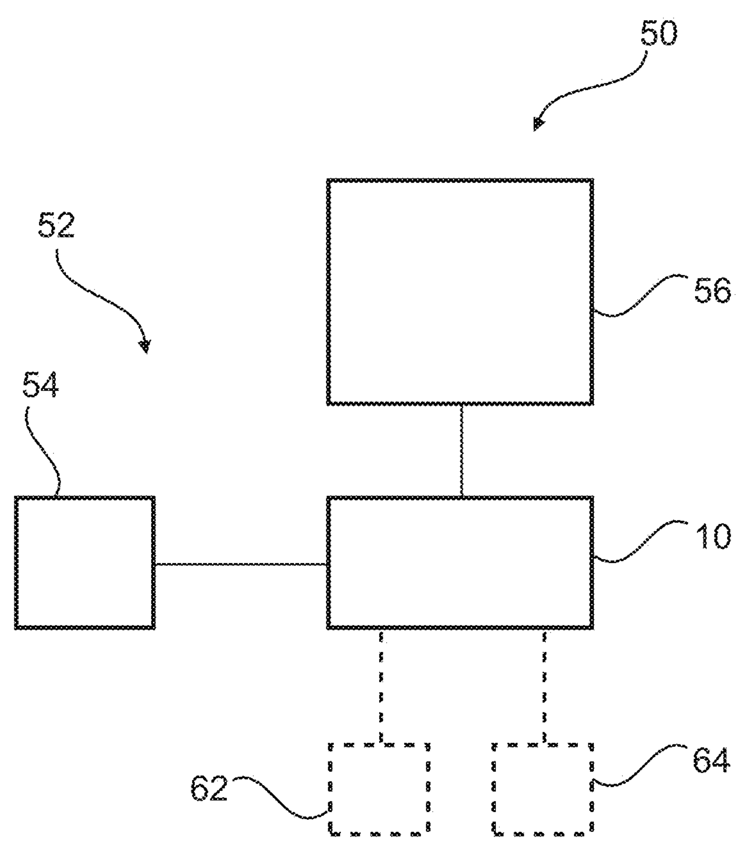
FIG. 2 shows an example of a system for determining a renal response index.

FIG. 2 shows an example of a system 50 for determining a renal response index. The system 50 comprises a measuring arrangement 52 with at least one sensor element configured to measure at least one physiological parameter of the subject's renal vasculature. The system 50 also comprises a device 10 for determining a renal response index according to one of the preceding examples. The system 50 further comprises a display device 56. The measuring arrangement 52 is configured to provide the value of at least one first measurement and the value of at least one second measurement to the classifying device.

The display device 56 is configured to display at least the renal response index generated by the classifying device.

Figure 3:
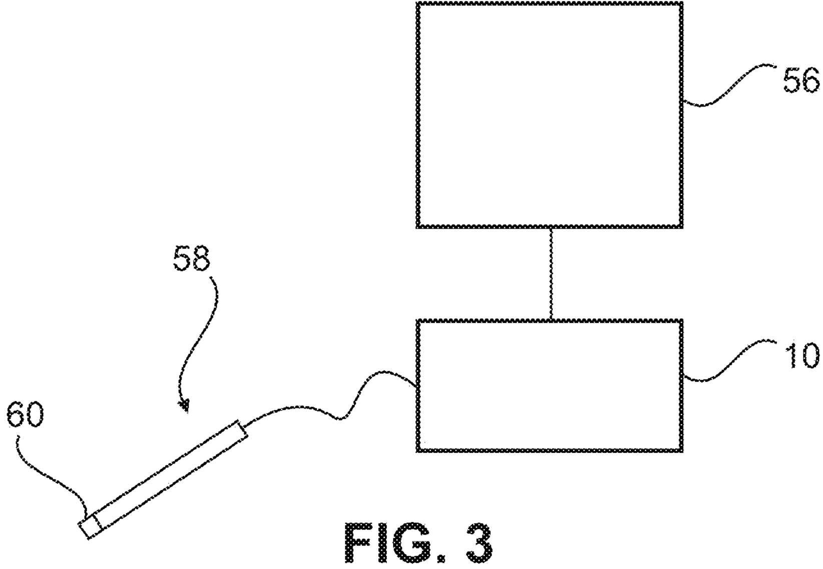
FIG. 3 shows another example of the system of FIG. 2.

FIG. 3 shows an option where the measuring arrangement 52 comprises an intravascular device 58 with at least one sensor element 60 configured to be inserted into a vascular structure of a subject and to measure the at least one physiological parameter of the subject's renal vasculature.

In another option, not shown in detail, the measuring arrangement 52 comprises an extravascular imaging device configured to measure the at least one physiological parameter of the subject's renal vasculature via imaging.

In an option, shown in FIG. 2, the system 50 also comprises a stimulation unit configured to provide electrical stimuli and/or to provide pharmaceutical stimuli by drug supply. The stimulation unit 62 may be integrated (not shown) with the measuring arrangement. As stimulation, one stimulus or a plurality of stimuli can be provided.

As an option, the stimulation unit is integrated with the intravascular device.

In another option, the stimulation unit is provided as a separate device.

In an example, a drug supply is provided by a device, such as an infusion apparatus or an inhaling device.

In another example, a drug supply is provided by a staff member, for example in form of a substance applied to the subject.

In an option, shown in FIG. 2, the system 50 also comprises an ablation unit 64 configured to provide renal ablation. The ablation unit 64 may be integrated (not shown) with the measuring arrangement.

In an option, the ablation unit is integrated with the intravascular device.

In another option, the ablation unit is provided as a separate device.

In a further option, the system comprises both the stimulation unit and the ablation unit. In an example, the stimulation unit and the ablation unit are both provided as separate units. In another example, one of the stimulation unit and the ablation unit is provided as a separate unit and the other one of the stimulation unit and the ablation unit is provided as an integrated unit. In a further, the stimulation unit and the ablation unit are both provided as integrated units.

In another option, not shown in detail, the system 50 is configured to provide an initial renal response index before an ablation process, and to provide a further renal response index after at least a first part of an ablation process. A success index is provided based on a ratio of the further renal response index and the initial renal response index.

FIG. 4*a* shows basic steps of an example of a method 100 for determining a renal response index, the method comprising the following steps.

In a first step 102, also referred to as step a1), a value of at least one first measurement of a physiological parameter of a subject's renal vasculature under a first condition is provided.

In a second step 104, also referred to as step c1), a value of at least one second measurement of a physiological parameter of the renal vasculature under a second condition is provided. In the second condition, a predetermined stimulation is provided. The first condition is non-stimulated or at least differently stimulated.

In a third step 106, also referred to as step d), a renal response index is generated based on the values of the at least one first and at least one second measurements. In an exemplary embodiment, a ratio between the at least one second measurement and the at least one first measurement is determined and a renal response index is generated based on the determined ratio and the pre-determined stimulation.

In a fourth step 108, also referred to as step e), the renal response index is provided and/or a classification into at least two groups of subjects is provided.

The method for determining a renal response index can also be referred to as "classification method for determining a renal response index".

The first measurement and the second measurement are taken in a sequential manner. In an example, the first measurement is taken before the second measurement. In another example, the second measurement is taken before the first measurement.

The non-stimulated, less stimulated or differently stimulated condition can also be referred to as baseline condition of the subject.

FIG. 4*b* shows another example of the method 100, wherein, between steps a1) and c1), it is further provided a step b) of stimulating 110 the renal vasculature by at least one of the group of a physical manoeuver, a pharmaceutical stimulus and an electrical stimulus.

FIG. 4*c* shows a further example of the method 100, where it is further provided a step a2) of displaying 112 the value of the at least one first measurement. In addition, or alternatively, it is provided a step c2) of displaying 114 the value of the at least one second measurement.

In another option, provided in addition or alternatively, it is further provided a step f) of indicating 116 if the generated renal response index is below or above a pre-determined threshold value, which threshold value is indicating a possible suitability for renal denervation.

In an example, not further shown, a further value of a further first measurement of a further physiological parameter of the subject's renal vasculature under the first condition is provided; and a further value of a further second measurement of a further physiological parameter of the renal vasculature under the second condition is also provided. A ratio between the further second measurement and the further first measurement is determined. The renal response index is generated based on the determined ratio between the at least one second measurement and the at least one first measurement, the determined ratio between the further second measurement and the further first measurement and the pre-determined stimulation.

In an example, also not further shown, the first measurement under the first condition is provided for the left renal artery and for the right renal artery; and the second measurement under the second condition is provided for the left renal artery and for the right renal artery. A ratio between the second measurement and the first measurement is determined separately for each of the left and right renal arteries, and a respective index is generated separately for each of the left and right renal arteries.

In addition, or alternatively, an average ratio between the second measurement and the first measurement is determined for the left and right renal arteries and the index is generated based on the average ratio.

In an option, the results for both renal arteries, i.e. the left index and the right index, are shown separately, and the average result, i.e. a common index, is also shown.

A measure for vascular health is pulse wave velocity (PWV). Pulse wave velocity is defined as the speed at which the pressure/flow pulse travels from the aorta to any peripheral vessel; the stiffer the vessel, the faster the pulse wave velocity. In an example, to determine pulse wave velocity, the arrival time of the cardiac pulse wave is measured at two distinct sites, e.g. the carotid and femoral arteries, and the difference between the arrival times is measured. By measurement or approximation of the distance between the two sites, the pulse wave velocity can be estimated.

Sympathetic overdrive, as mentioned, may cause peripheral and renal artery vasoconstriction. Vasoconstriction increases the stiffness of the vessel and therefore should be associated with a 'locally' increased pulse wave velocity. The pulse wave velocity inside the renal artery in patients with resistant hypertension can be very high; more than 20 m/s, which makes it difficult to determine the pulse wave velocity in the relatively short renal arteries (2 to 6 cm).

Clinical data suggests that certain physiology parameters, among which is the velocity of the pressure/flow pulse (pulse wave velocity) in the renal artery as well as the flow resistance in the intrarenal vasculature pre-treatment, are useful to predict the outcome of renal denervation.

In an example, renal arterial resistance and pulse wave velocity measured in the vessel is used during renal denervation to 1.) predict responders before renal denervation therapy, as well as to 2.) assess success of the renal denervation ablation.

Since there is no "normal" or standard value for pulse wave velocity (or any other renal hemodynamic parameter) in the renal artery, the value associated with sympathetic overdrive is difficult to determine. In an example, sympathetic tone and therefore the hemodynamic properties of the kidneys and the renal arteries can be changed by drugs or other stimuli. Since suitable patients for renal denervation have sympathetic overdrive, stimulation of the sympathetic nerves in these patients should have limited effect on renal hemodynamics as they are already in a state of over-activity. Therefore, the change in renal hemodynamics between baseline and after giving sympathetic stimulation contains information to distinguish between those patients already in a sympathetic overdrive state (likely responders to renal denervation) and those who do not have sympathetic overdrive (likely non-responders).

Furthermore, the hemodynamic parameter in the left and right kidney may vary, a therapy decision based on measurements performed in only one renal artery could be inappropriate. A measurement in both renal arteries may indicate a left/right asymmetry in the hemodynamic parameter, which may require a modified therapy decision.

Physiological parameters such as pressure, flow, pulse wave velocity or resistance show variability, particularly when measured in two different renal vessels or over longer time scales. Each measurement in a given renal vessel by minimally invasive approach may give a different measure, making a single measurement of pulse wave velocity or resistance in a single renal artery difficult to interpret.

In an example, multiple measurements are combined done at different times, at different positions, in different renal arteries, before, during or after various stimuli into a composite index number. This index is less susceptible to natural variations than single measurement values. The index facilitates treatment decision, for example by defining a threshold beyond which treatment is advisable.

Well-defined manoeuvers like pharmacological stimuli, physical manoeuver and/or electrical stimulation of the sympathetic nervous system enable a better stratification to distinguish between sympathetic related hypertension and other kidney diseases.

A change of the pulse wave velocity or the resistance/impedance can be caused by a sympathetic hyperactivity, an increased venous pressure, a structural vascular change (e.g. stenosis), swelling of the kidney (e.g. hydronephrosis). The two last-mentioned may also affect only one kidney.

Due to these multiple causes, which all may alter the hemodynamic parameter, a manoeuver-based analysis enables a better stratification.

In an example, a measure of the total vascular resistance covers the geometry of the renal vessels, the perfusion in the kidney and the venous blood pressure.

A measure of the total vascular resistance covers the stiffness of the artery, the perfusion in the kidney and the venous flow. By the previously mentioned manoeuvers, the role can be identified of the sympathetic activity and the impact of the arterial stiffness. The calculated indices will be specific for the renal denervation therapy decision.

Multiple measurements may be recorded using the device measuring the pulse wave velocity or the resistance/impedance inside the vessel with at least one sensor. If only a single measurement is performed, the system acquires and records the measure. A value representative of the measurement results is displayed on the system.

When a second measure is recorded in the bilateral/opposite vessel, a second value is displayed, and an average value representative of the measurements on both sides is also displayed.

The same may be repeated before/after and during a physical manoeuver or other sympathetic stimulation to evaluate the effect on the hemodynamic parameter pressure, pulse wave velocity and impedance.

The same may be repeated at a later stage after treatment to evaluate the effect of the therapy and compare the measured values before and after the therapy in a single vessel or on both vessels.

In an example, it is provided:

An intravascular wire or catheter with at least one sensor element measuring pressure, flow, electric impedance and/or vessel geometry.

A stimulation device providing stimulation of the kidneys, the renal arteries or the nervous system using physical manoeuver and/or pharmaceutical stimuli and/or electrical stimuli.

A system that records a measure using the device sensing element in the first renal vessel; and that records a further measure when the renal vessel is stimulated by one or multiple stimulation devices; and that displays result of the first renal artery on the system together with a threshold value or an indicator as to whether the patient is suitable for renal denervation.

As optional elements, it is provided:

A system that determines an index describing the properties of the first renal vessel based on the measurement recorded by the device; and that displays the index on the system together with a threshold value or an indicator as to whether the patient is suitable for renal denervation.

A system that records another measure in the second contra-lateral renal artery without stimulation; and that records a further measure when stimulated by one or multiple stimulation devices that determines the index in the second renal vessel based on the measurement recorded by the device; and that displays result of the second renal and an average based on both (left and right) measurements on the system; and that determines the index of the measures in the two opposite vessels, both with and without a stimulation by the stimulation devices.

A system that repeats the above measurements and index calculation to determine ablation success.

An intravascular device as described above where a stimulation unit (e.g. for electrical stimulation) is integrated.

An intravascular device as described above where an ablation unit for renal denervation is integrated.

An intravascular device as described above where a stimulation unit (e.g. for electrical stimulation) and an ablation unit for renal denervation are integrated.

In an example, a system is provided that can be used to test the likelihood of response to renal denervation (RND) by measuring the renal pulse wave and/or physiological response to a stimulus of the sympathetic nervous system.

Proposed stimuli are delivered by a stimulation device. These stimulation devices can be at least one of the following techniques: a) physical maneuvers, and/or b) pharmaceutical stimuli, and/or c) electrical stimuli.

Such stimuli may be a particular vasodilating drug (dopamine, nitrate, adenosine, etc.), a nerve neuromodulating drug (anesthetic/temporally sympathetic blocking drug, or sympathetic stimulating drug), or a handgrip performed/administered before or during the measurement or any other stimulus affecting sympathetic response.

A physical maneuver could be a compression maneuver that impedes the systemic and venous blood flow in the peripheral vessel, or a respiration maneuver (e.g. Müller Maneuver, Valsalva maneuver) which impedes the central venous pressure and the intra-abdominal pressure, which acts as a modulated pressure on the kidneys and the renal vessels.

In an example, the response before/after and during stimulation is measured by arterial physiology (pressure, pulse wave velocity, resistance, flow, vessel geometry or combination), specifically in renal arteries. An index derived from these measurement is then used to stratify patients in at least two groups; with one of the group representing patients not likely to respond well to therapy.

Composite Hemodynamic Indices

Stimulation induced hemodynamic alteration indices will be determined based on the measurements before/after and during stimulation. The measurements will be done at one, two and/or multiple locations in the renal vascular structure.

Measurements will be done with or without gating to a further physiological parameter. One typical gating is a measurement synchronized to an ECG of the beating heart. This enables a measurement either in a reflection free period or at the maximal or minimal value of a physiological parameter.

In the examples below, a setup how to perform the measurements before/after and during stimulation is described in more detail.

By these examples, different stimulation induced hemodynamic alteration indices will be determined.

The determined composite hemodynamic indices are:

vascular resistance alteration index;

renal flow alteration index;

pulse propagation index; and pulse reflection index.

In the determination of the indices, a drug induced stimulation, an electrical stimulation, a physical maneuver or a combination of different stimuli are applicable. When the term stimulation is used in the following, the stimulation can be a single or a combination of multiple stimuli.

In an example, the pulse propagation index is provided as a pulse propagation alteration index.

In an example, the pulse reflection index is provided as a pulse reflection alteration index.

For each index, a cutoff value will be defined, which describes whether a patient will benefit from renal denervation therapy.

Vascular resistance index: To determine the effect of the arterial stiffness of the renal arteries, a vascular resistance alteration index is determined as the ratio of the vascular resistance (R=perfusion pressure/flow) during a stimulation with respect to a reference value determined without a stimulus:

$$\text{Vascular Resistance Alteration Index} = R_{stim}/R_{ref}$$

respectively for multiple stimuli:

$$\text{Vascular Resistance Alteration Index} = R(_{stim\_1+stim\_2+\ldots+stim\_n})/R_{ref}$$

In an example, to determine the effect of sympathetic activity on the renal vascular resistance, the vascular resistance alteration index is determined as the ratio of the vascular resistance (R=perfusion pressure/flow) during a stimulation with respect to a reference value determined without a stimulus.

If the value of the determined index is below a certain threshold, the patient is a likely renal denervation responder. The value depends on the type and doses of stimulation. A quantified value can only be given as an example for a certain stimulation.

The stimulation can be done by different agents and different drug doses. It is common for all drugs that they interact as neurotransmitter with receptors but in a different manner. Some drugs are interacting mostly with Alpha receptors, others interact with Beta receptors, respectively with both. From a hemodynamic perspective, some drugs are vaso-active (dilating or constricting arteries) others are cardio-active (increasing the cardiac output and the systemic blood pressure). All types of drugs will alter differently the blood pressure, the renal blood flow and the renal pulse wave velocity. For each a dedicated index and a corresponding threshold value will be defined.

Sympathetic overdrive causes peripheral vasoconstriction. In the kidney, this therefore decreases renal blood flow as the renal artery is constricting. A renal sympathetic hyperactivity can be considered as a renovascular disease impeding the renal flow. A vasodilating stimulation increases the flow or vice versa requesting a lower perfusion pressure to achieve a comparable renal blood volume.

An example for a drug stimulation by a sympathetic stimulating drug (e.g. epinephrine) is provided: A value smaller than 1.2 can be considered for recommending a renal denervation therapy.

In a similar way, a value above 0.8 can be considered for recommending for a renal denervation therapy, when using a sympathetic blocking drug (e.g. phentolamine).

The thresholds value is only an example and can also be set differently.

Renal flow alteration index: The index determines the effect of a stimulation or a combination of multiple stimuli on the flow rate (specified as a change of the renal minute volume).

The renal flow index is determined as the ratio of the renal flow during a stimulation (or multiple stimuli) with respect to a reference value determined without a stimulus:

$$\text{Renal Flow Index} = F_{stim}/F_{ref}$$

respectively for multiple stimuli:

$$\text{Renal Flow Index} = F(_{stim\_1+stim\_2+\ldots+stim\_n})/F_{ref}$$

If the value of the determined index is above a certain threshold, the patient is a candidate for an effective renal denervation therapy.

A value above 0.8 can be considered for recommending a renal denervation therapy, when using a sympathetic stimulating drug (sympathicomimetic, e.g. epinephrine).

In similar way, a value above 1.2 can be considered for recommending a renal denervation therapy, when using a sympathetic blocking drug (e.g. phentolamine).

The thresholds value is only an example and can also be set differently.

Pulse propagation index: The index determines the effect of a stimulation or a combination of multiple stimuli on the pulse propagation in the renal arteries. The index determines the change of the pulse wave velocity.

The pulse Propagation index is determined as the ratio of the renal flow during a stimulation (or multiple stimuli) with respect to a reference value determined without a stimulus:

$$\text{Pulse Propagation Index} = PVW_{stim}/PVW_{ref}$$

respectively for multiple stimuli:

$$\text{Pulse Propagation Index} = PWV(_{stim\_1+stim\_2+\ldots+stim\_n})/P_{ref}$$

Vasoconstriction is associated with a stiffening of the vessel wall. Therefore, the pulsatile movement of the pressure wave of the blood through the vessels is expected to move faster. In patients suitable for renal denervation, it is expected that the increase in stiffness and therefore pulse wave velocity after additional sympathetic stimulation is not that big and therefore the ratio will only be slightly above 1. For patients who do not have sympathetic overdrive causing their hypertension the sympathetic stimulating drug (e.g. epinephrine) will cause vasoconstriction and thus a larger increase in $PVW_{(stim)}$ and in the pulse propagation index.

A value below 1.2 can be considered for recommending a renal denervation therapy, when using sympathetic stimulating drug (sympathicomimetic, e.g. epinephrine).

In a similar way, a sympathetic blocking drug (e.g. phentolamine) can be used in the inverse way. A value above 0.8 can then be considered for recommending a renal denervation therapy, when using a sympathetic blocking drug.

If the value of the determined index is above a certain threshold, the patient is a candidate for an effective renal denervation therapy.

The thresholds value is only an example and can also be set differently.

Pulse reflection index: The index determines the effect of a stimulation or a combination of multiple stimuli on the pulse reflection at the renal vascular bed measured in the renal arteries. The index determines the change of the pulse rise time and the attenuation of the pulse amplitude.

The pulse transfer time is shorter than the pulse rise time in the renal arteries due to the short length of the renal arteries. Therefore, the pulse reflection index is determined in the time domain by the change of the rise time and pulse shape.

The pulse reflection index is determined as the ratio of the renal flow during a stimulation (or multiple stimuli) with respect to a reference value determined without a stimulus:

$$\text{Pulse Reflection Index} = P_{rise\ time(stim)}/P_{rise\ time(ref)}$$

respectively for multiple stimuli:

$$\text{Pulse Reflection Index} = P_{rise\ time(stim\_1+stim\_2+\ldots+stim\_n)}/P_{rise\ time(ref)}$$

A value below 1.2 can be considered for recommending a renal denervation therapy, when using a sympathetic stimulating drug.

In a similar way, a sympathetic blocking drug (e.g. phentolamine) can be used in the inverse way. A value above 0.8 can then be considered for recommending a renal denervation therapy, when using a sympathetic blocking drug.

If the value of the determined index is above a certain threshold, the patient is a candidate for an effective renal denervation therapy.

Figure 5A:
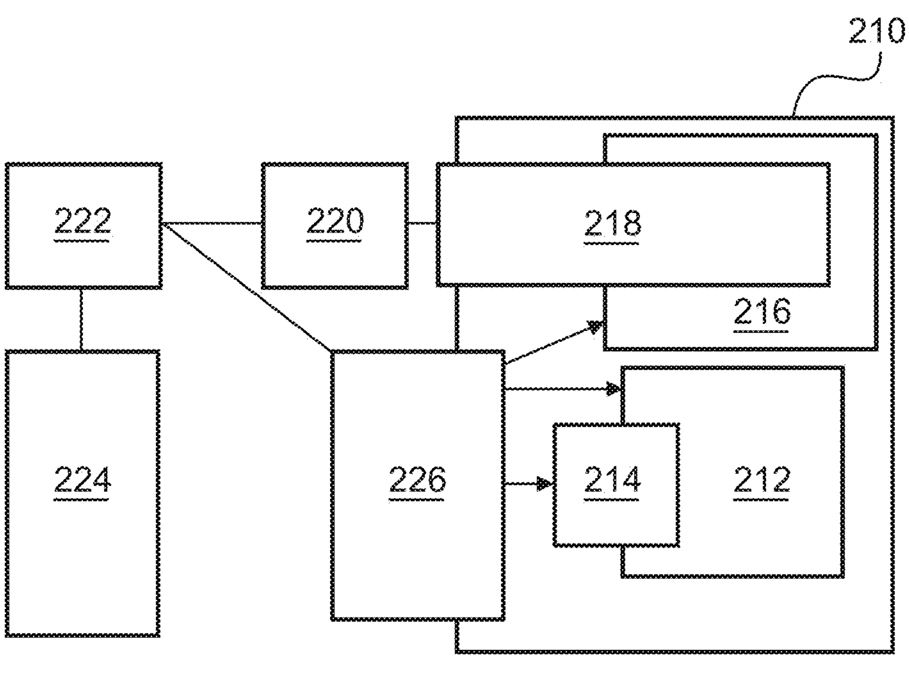
FIG. 5*a* schematically shows elements of another example of a setup for determining a renal response index.
Figure 5B:
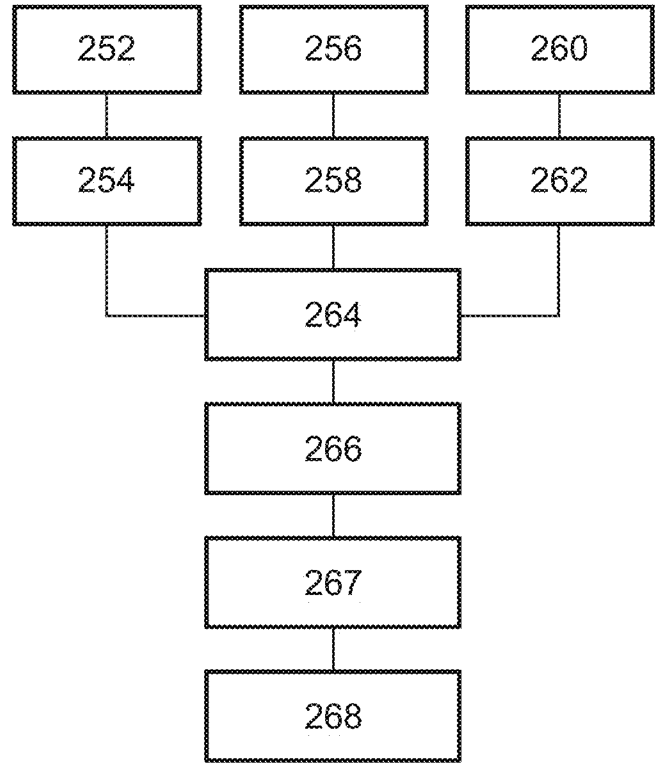
FIG. 5*b* schematically shows a flow chart of data acquisition and processing for the example of FIG. 5*a*.

A schematic depiction and a flow chart of another example are shown in FIG. 5*a* and in FIG. 5*b*. The example comprises an intravascular device (elongated member) with at least one pulse wave velocity sensor element that records pulse wave velocity in a renal artery. After this measurement is done, a stimulation technique is used to stimulate the renal system. Preferably, this stimulation technique is integrated into the same intravascular device, for example, a catheter with a drug delivery lumen. During the stimulation, the intravascular device records the $PWV_{stim}$. A processing unit processes the raw measurement into two values that are indicative of the pulse wave velocity in rest and during stimulation. For example, the two recordings are synchronized with the ECG and the pulse wave velocity value for the two different states is determined by averaging a number of cycles. A displaying unit displays the results together with an indicator as to whether the patient is suitable for renal denervation.

FIG. 5*a* schematically shows the elements and FIG. 5*b* schematically shows the flow chart of the data acquisition and processing of the example of FIG. 5*a*.

A first frame indicates a subject 210 with kidney(s) 212 and a smaller frame is indicating a nerve system 214. A further frame above the kidney 212 indicates a renal artery 216. A measurement device 218 is indicated as providing data from the renal artery 216. The measurement device 218 is shown as being partly inserted into a vascular structure of the subject 212. A data acquisition/recording unit 220 is at least data-connected to the measurement device 218. The data acquisition/recording unit 220 is at least data-connected to a processing unit 222. A console/display 224 is connected to the processing unit 222. The processing unit 222 is also connected to one or more stimulation units 226 that may act on the nerve system 214, the kidney(s) 212 and/or the renal artery 216.

In the flow chart, a first condition 252 results in a first measurement 254, and a second condition 256 results in a second measurement 258, and an nth condition 260 results in an nth measurement 262. The measurements 254, 258, 262 are subject to signal processing 264. Next, a display 266 of the measures is provided. Further, an interpretation and recommendation 268 is provided.

Figure 6A:
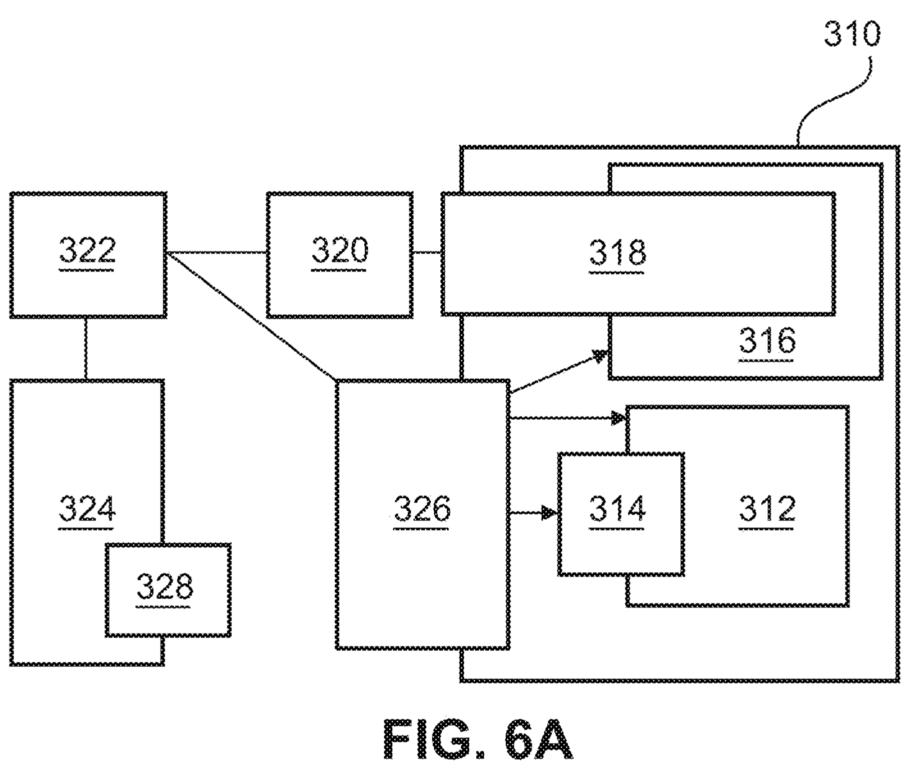
FIG. 6*a* schematically shows elements of a further example.
Figure 6B:
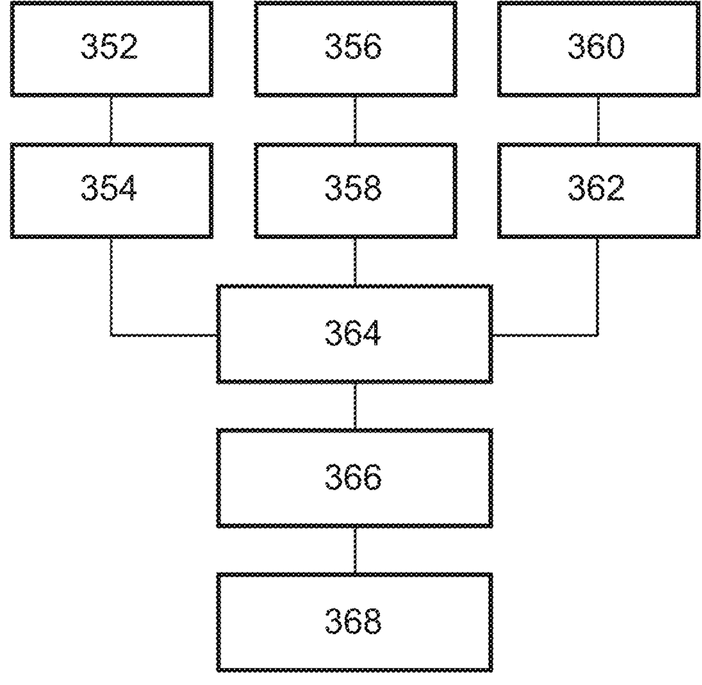
FIG. 6*b* schematically shows a flow chart for the example of FIG. 6*a*.

A schematic depiction and a flow chart of another example are shown in FIG. 6*a* and FIG. 6*b*. This example is similar to the example above, except that the two (or more) measurements are further condensed into a single index value. An index value can be used in combination with a threshold value to guide treatment decision. The index can be calculated by the ratio of the two measurements or by another predefined algorithm. Optionally, the index calculation can be determined by a sequence of measurements done at different levels of stimulation and/or points in time.

FIG. 6*a* schematically shows the elements and FIG. 6*b* schematically shows the flow chart of the data acquisition and processing of the example of FIG. 6*a*.

FIG. 6*a* shows similar features as FIG. 5*a*. A first frame indicates a subject 310 with kidney(s) 312, a nerve system 314 and a renal artery 316. A measurement device 318 is also provided, connected to a data acquisition/recording unit 320, which is connected to a processing unit 322. A console/display 324 is also provided. One or more stimulation units may act on the patient 310. As indicated above, an index 328 is shown.

In the flow chart, a first condition 352 is used for a first measurement 354, a second condition 356 for a second measurement 358, and an nth condition 360 for an nth measurement 362, the measurements 354, 358, 362 being subject to signal processing 364. Following, a display 366 of the measures is provided, but followed by a calculation 367 of the index. Further, an interpretation and recommendation 368 is provided as above.

Figure 7:
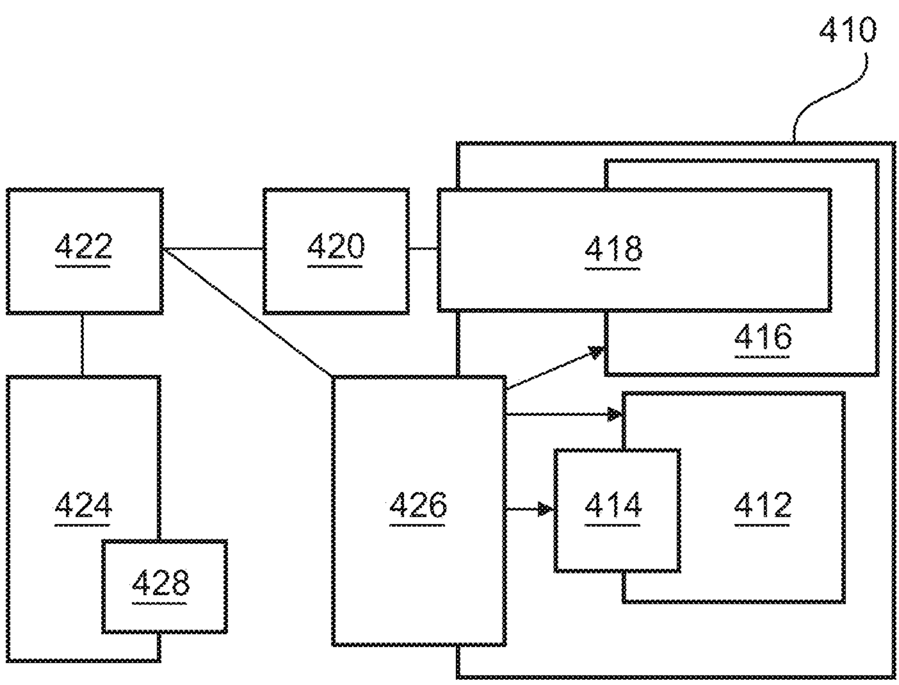
FIG. 7 schematically shows elements of a still further example.

A schematic depiction of another example is shown in FIG. 7, which is similar to the two examples above of FIGS. 5*a*/5*b* and FIGS. 6*a*/6*b*, except that a drug delivery device is used to test the sympathetic and hemodynamic response to drug induced neural modulation and change of vascular properties by measuring the renal pulse wave and pressure, flow and impedance.

FIG. 7 schematically shows the elements; the respective flow chart is not shown.

A subject 410 with kidney(s) 412, a nerve system 414 and a renal artery 416 is shown. A measurement device 418 is provided connected to a data acquisition/recording unit 420, which is connected to a processing unit 422 and a console/display 424 that may show an index 428. As stimulation unit, a drug delivery unit 426 is provided.

Figure 8:
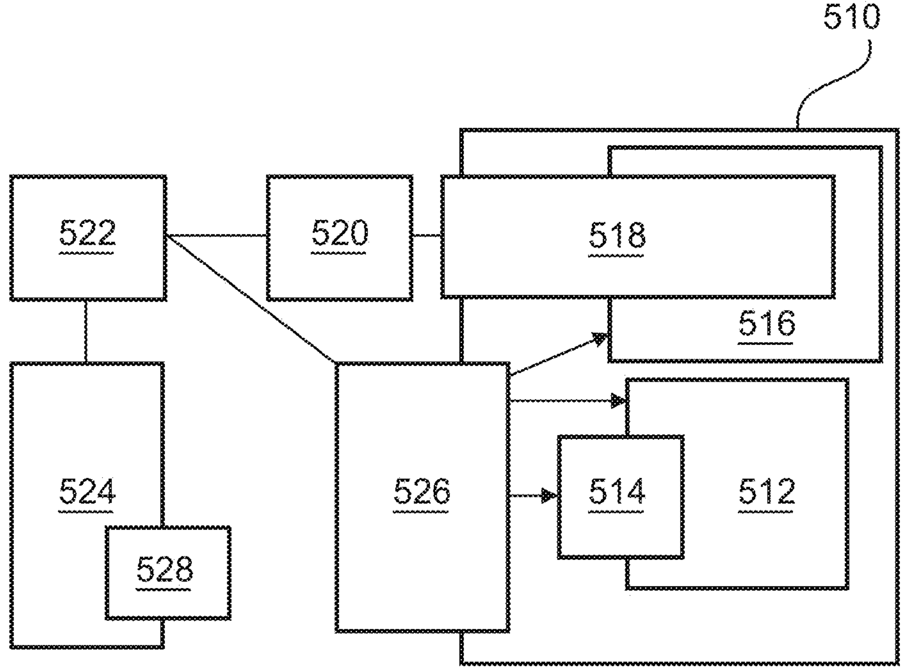
FIG. 8 schematically shows elements of another example.

A schematic depiction of another example is shown in FIG. 8 that is similar to the two examples above of FIGS. 5*a*/5*b* and FIGS. 6*a*/6*b*, except that a stimulus by an energy delivery device is administered in the renal vessels respectively in the kidney tissue. The energy can be e.g. electrical energy, thermal energy, light energy, or ultrasound energy.

FIG. 8 schematically shows the elements; the respective flow chart is not shown.

A subject 510 with kidney(s) 512, a nerve system 514 and a renal artery 516 is shown. A measurement device 518 is provided connected to a data acquisition/recording unit 520, which is connected to a processing unit 522 and a console/display 524 that may show an index 528. As stimulation unit, a stimulator in form of an energy delivery device 526 is provided.

Figure 9:
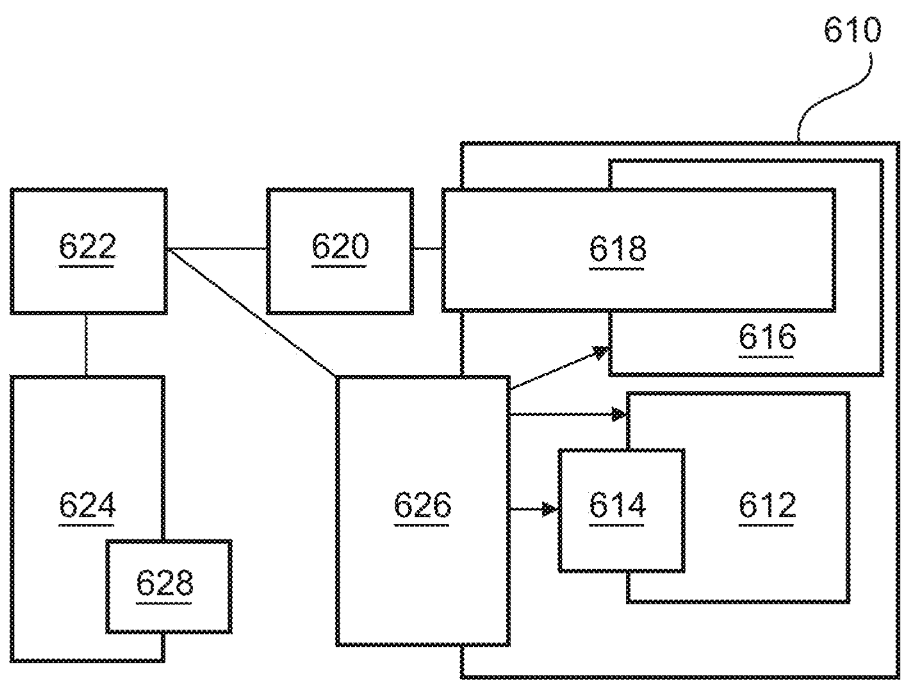
FIG. 9 schematically shows elements of a further example.

A schematic depiction of another example is shown in FIG. 9. This example is similar to the two examples above of FIGS. 5*a*/5*b* and FIGS. 6*a*/6*b*, except that the stimulation is effected in the form of physical maneuver or activity such as a handgrip or another physical activity of the patient.

FIG. 9 schematically shows the elements; the respective flow chart is not shown.

A subject 610 with kidney(s) 612, a nerve system 614 and a renal artery 616 is shown. A measurement device 618 is provided connected to a data acquisition/recording unit 620, which is connected to a processing unit 622 and a console/display 624 that may show an index 628. As stimulation unit, a body stimulation 626 in form of a handgrip is provided.

Figure 10:
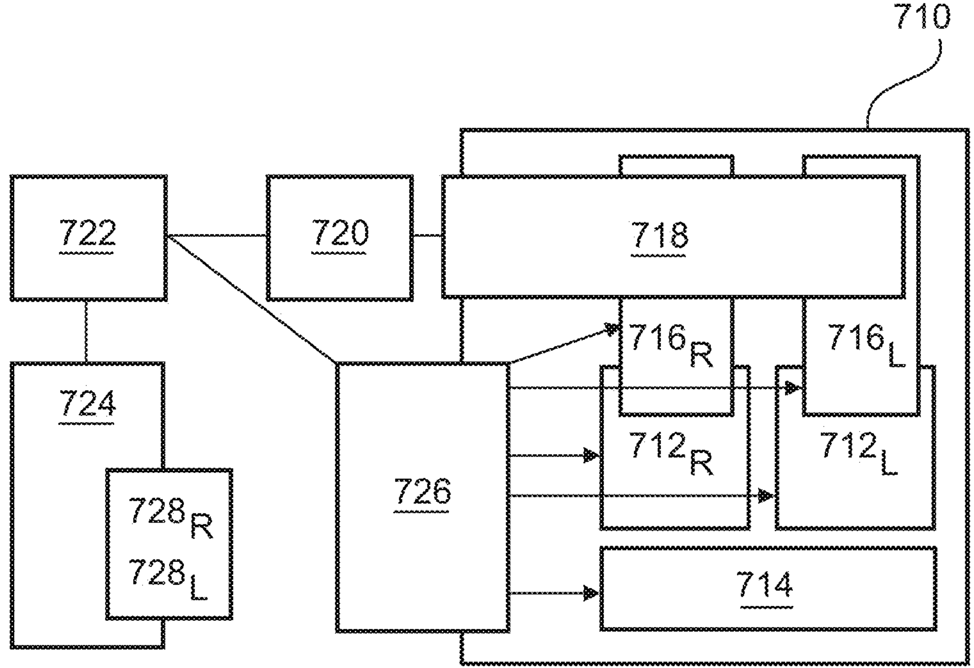
FIG. 10 schematically shows elements of another example.

A schematic depiction of another example is shown in FIG. 10. This example is similar to the five examples above (FIGS. 5*a*/5*b*, FIGS. 6*a*/6*b*, FIG. 7, FIG. 8 and FIG. 9), except that the measurement is done both in the left and in the right renal artery to determine an index of response difference in the two kidneys. The likelihood of response is assessed based on measurements in each of the two kidneys (with at least one measure per kidney). The processing unit will determine and display information on both kidneys and based on that give treatment guidance which may include: treat both renal arteries, treat only the right renal artery, treat only the left renal artery and don't treat.

FIG. 10 schematically shows the elements; the respective flow chart is not shown.

A subject 710 with a nerve system 714 and a renal artery 716 is shown. A measurement device 718 is provided connected to a data acquisition/recording unit 620, which is connected to a processing unit 722 and a console/display 724. A stimulation unit is also provided. The subject is shown with a right kidney $\mathbf{714}_R$ and a left kidney $\mathbf{714}_L$, as well as with a right renal artery $\mathbf{716}_R$ and a left renal artery $\mathbf{716}_L$. The console/display 724 shows a right kidney index $\mathbf{728}_R$ and a left kidney index $\mathbf{728}_L$.

In a further example, not shown, a system is provided similar to those described in the six examples above where a stimulation unit (e.g. for electrical stimulation) is integrated into the intravascular device.

In a further example, not shown, a system is provided similar to those described in the examples above where an ablation unit for renal denervation is integrated in the intravascular device.

In a further example, not shown, a system is provided similar to those described in the examples above where a stimulation unit (e.g. for electrical stimulation) and an ablation unit for renal denervation are integrated.

In a further example, not shown, a system is provided similar to those described in the examples above where the measurements can be repeated after (partial) ablation of nerves and where the processing unit will provide a measure of treatment success to help the interventionist to decide whether to stop or to continue the treatment.

In a further example, not shown, a system is provided similar as the previous examples, except that the measurement device is located in a non-renal artery, that is also affected by sympathetic over-activity. Examples of such arteries are e.g. tibial, femoral popliteal, brachial and radial/ulnar. The hemodynamic measurements are therefore measured in the non-renal artery and the measured index is then used to determine if the subject is a candidate for an effective denervation therapy.

In another exemplary embodiment of the present invention, a computer program or a computer program element is provided that is characterized by being adapted to execute the method steps of the method according to one of the preceding examples, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus, comprising:

an intravascular catheter or guidewire configured to be positioned within a renal artery of a subject, wherein the intravascular catheter or guidewire comprises a sensor configured to measure a physiological parameter of the renal artery; and a controller comprising at least one of a processor, an application specific integrated circuit (ASIC), or a field-programmable gate array (FPGA), wherein the controller is configured to:

control the intravascular catheter or guidewire to:

obtain, with the subject under no stimulation or a first stimulation, a first measurement of the physiological parameter for the renal artery while positioned in the renal artery, wherein the no stimulation or the first stimulation is distinct from renal denervation; and obtain, with the subject under a second stimulation, a second measurement of the physiological parameter for the renal artery while positioned in the renal artery, wherein the second stimulation is distinct from the renal denervation;

determine a ratio for the renal artery using the first measurement and the second measurement;

generate a renal response index for the renal artery based on the ratio; and provide the renal response index to a display, wherein the first and second measurements are obtained, the ratio is determined, and the renal response index is generated and provided to the display before the renal denervation is performed.

2. The apparatus of claim 1, wherein the physiological parameter comprises pulse wave velocity.

3. The apparatus of claim 2, wherein the second stimulation is configured to cause a hemodynamic alteration for the subject such that the renal response index comprises a pulse propagation alteration index.

4. The apparatus of claim 1, wherein the physiological parameter comprises vessel impedance.

5. The apparatus of claim 4, wherein the second stimulation is configured to cause a hemodynamic alteration for the subject such that the renal response index comprises a vascular impedance alteration index.

6. The apparatus of claim 1, wherein the controller is configured to:

determine whether the subject is suitable for the renal denervation based on at least one of the renal response index; and provide, to the display, an indicator representative of whether the subject is suitable for the renal denervation.

7. The apparatus of claim 6, wherein, to determine whether the subject is suitable for the renal denervation, the controller is configured to provide a classification of the subject into one of at least two groups.

8. The apparatus of claim 6, wherein, to determine whether the subject is suitable for the renal denervation, the controller is configured to determine if the renal response index is below or above a pre-determined threshold value.

9. The apparatus of claim 1, wherein the second stimulation comprises at least one of a physical maneuver, a pharmaceutical stimulation, or an electrical stimulation.

10. The apparatus of claim 1, wherein the controller is configured to:

receive, with the subject under no stimulation or the first stimulation, a further first measurement of a further physiological parameter;

receive, with the subject under the second stimulation, a further second measurement of the further physiological parameter; and generate the renal response index based on the further first measurement and the further second measurement.

11. The apparatus of claim 1, further comprising:

the display.

12. The apparatus of claim 1, wherein the controller is configured to control providing at least one of the first stimulation or the second stimulation to the subject.

13. The apparatus of claim 12, wherein, to control providing at least one of the first stimulation or the second stimulation, the controller is configured to control at least one of providing an electrical stimulation or providing a pharmaceutical stimulation to the subject.

14. The apparatus of claim 1, wherein the controller is configured to control providing the renal denervation to the subject.

15. The apparatus of claim 14, wherein, to control providing the renal denervation to the subject, the controller is configured to control providing ablation to the subject.

16. The apparatus of claim 1, wherein controller is configured to:

generate a further renal response index after at least a part of the renal denervation; and generate a success index is based on the further renal response index and the renal response index.

17. The apparatus of claim 6, wherein a relatively smaller magnitude of change between the first measurement and the second measurement is configured to indicate that the subject is in sympathetic overdrive and suitable for the renal denervation, wherein a relatively larger magnitude of change between the first measurement and the second measurement is configured to indicate that the subject is not in the sympathetic overdrive and not suitable for the renal denervation.

* * * * *